United States Patent

Bates

[11] Patent Number: 4,693,712
[45] Date of Patent: Sep. 15, 1987

[54] BACTERICIDE VALVE ON FLUID COLLECTION BAG

[75] Inventor: David Bates, Libertyville, Ill.

[73] Assignee: The Kendall Company, Boston, Mass.

[21] Appl. No.: 798,209

[22] Filed: Nov. 14, 1985

[51] Int. Cl.⁴ .............................................. A61M 1/00
[52] U.S. Cl. ................................... 604/323; 604/335; 604/350; 137/268
[58] Field of Search ............... 604/322, 323, 335, 350, 604/317; 422/28, 261, 276, 277; 210/198.1, 347; 137/246, 268; 128/760, 762, 766, 767

[56] References Cited

U.S. PATENT DOCUMENTS

| | | | |
|---|---|---|---|
| 4,249,562 | 2/1981 | King, Sr. | 137/268 |
| 4,417,892 | 11/1983 | Meisch | 604/323 |
| 4,460,362 | 7/1984 | Bates | 604/323 |

FOREIGN PATENT DOCUMENTS 1261635  1/1972  United Kingdom ................ 137/268

Primary Examiner—C. Fred Rosenbaum
Assistant Examiner—J. L. Kruter
Attorney, Agent, or Firm—Donald N. Halgren

[57] ABSTRACT

A liquid collection system for collecting and discharging urine from a catheterized patient. A collection bag receives urine through the catheter, and has a drain system therein, which comprises a valve having a bactericide element over which the urine must flow as it is being drained from the bag. The bactericide element is held in an openable cage, so as to permit replacement of the bactericide element as an "as needed" basis. The bactericide disposed within the valve helps prevent retrograde contamination of the liquid collection system.

8 Claims, 5 Drawing Figures

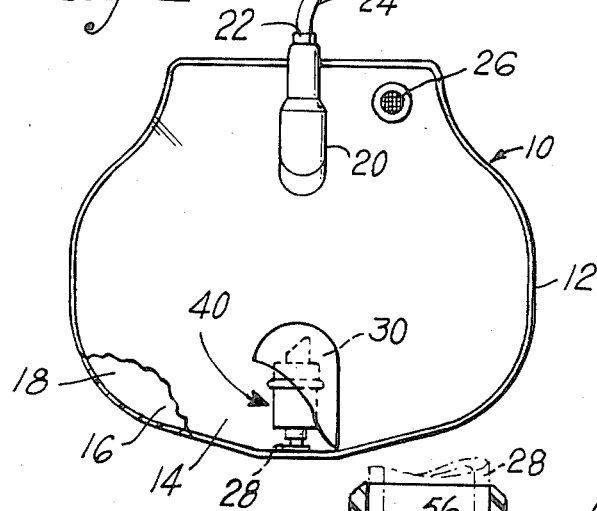
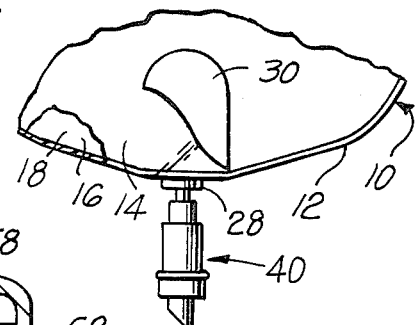
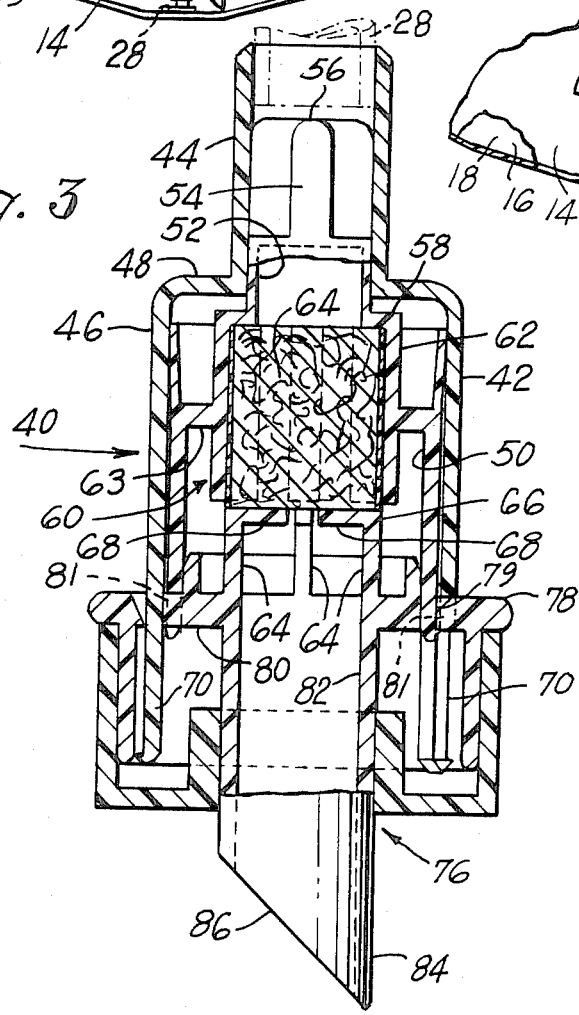

BACTERICIDE VALVE ON FLUID COLLECTION BAG

BACKGROUND OF THE INVENTION

This invention relates to collection containers for medical liquids, and more particularly to disposal valves on those collection containers.

PRIOR ART

Liquid drainage systems are an adjunct part of medical liquid collection systems. These collection systems are generally used for draining urine from the bladder of a patient. Such collection systems generally comprise a catheter having a distal end received in the bladder of the patient, the catheter having a drainage tube connected to its proximal end thereof. A collection bag may be collected at its downstream end of the drainage tube, wherein the urine drains from the bladder through the catheter and then the drainage tube, into the collection bag for retention therein.

Such systems are intended to be maintained in a sterile condition and hence, are closed to the atmosphere to prevent the introduction therein of bacteria with subsequent possible harmful effects to the patient. An example of such a system, is shown in U.S. Pat. No. 3,312,221 to Overment. This particular system utilizes a flutter valve for drainage of the collection bag. Bactericide pellets are disposed within the bag to minimize retrograde infection through the catheter. Another drainage arrangement for a urine collection bag is shown in U.S. Pat. No. 4,462,510 to Steer et al., wherein a rotatable valve is disposed at the bottom of the urine collection bag which valve is readily disassembled.

A further collection bag valve system is shown in U.S. Pat. No. 3,529,599 to Folkman et al., which comprises a one-way disc valve at its outlet. This arrangement however does not include a bactericide element to prevent bacteria from entering the collection bag itself. A still further attempt at having a drainage system for a urine bag is shown in U.S. Pat. No. 4,443,219 to Meisch et al., wherein two bags are utilized within the drainage system. This system utilizes the second bag to maintain the sterility of the primary collection bag. However, it fails to provide any bactericide to minimize the possibilities of contamination in the primary bag.

It is an object of the present invention to provide a simple drainage valve for a urine collection bag.

It is a further object of the present invention to provide a drainage bag with a bactericide therein to prevent contamination of the collection bag.

BRIEF SUMMARY OF THE INVENTION

The liquid collection system utilizing the present invention comprises a drainage container having a chamber for collection of a medical liquid therein such as urine, a flexible tubular section communicating with a lower portion of the chamber, and a valve arrangement disposed on the tubular section for releasably closing the tubular section. The valve arrangement also includes a bactericide, to prevent retrograde infection of the containment bag. The valve arrangement comprises a first housing having an upper cylindrical portion of a first diameter meeting with a second portion of the housing of a larger diameter. A piston is slidably disposed in the larger housing portion. The piston has flutes therein to permit the passage of liquid therethrough, when the piston has been moved from a shut-off position adjacent the first portion of the housing to an open position downstream in the larger housing. A chamber within the piston contains a bactericide pellet. The chamber is in fluid communication with the flutes of the piston so as to insure fluid communication between those flutes and the bactericide pellet within the chamber of the piston.

Axial displacement of the piston within the housing opens the valve to permit discharge of the containment bag through the flexible tubing and out through the valve. The fluid, in this case urine, is caused to pass across the bactericide pellet within the chamber so as to disinfect urine passing thereby. As the pellet is moistened, bactericide is liquified. This liquid bactericide acts to kill any bacteria attempting to enter the distal end of the valve and thus drainage system. In addition, because of the construction (center structure) of the valve, any potential bacteria must travel a torturous path around and through the liquid bactericide. The valve is shut by axial displacement over the piston within the housing configuration. The bactericide pellet acts to disinfect any urine remaining within the valve arrangement as the valve is closed. Thus retrograde infection is prevented by eliminating the possibility of infection passing from the valve back into the containment bag and possibly back through the catheter system and into the patient.

BRIEF DESCRIPTION OF THE DRAWINGS

The objects and advantages of the present invention become more apparent when viewed in conjunction with the following drawings, in which:

FIG. 1 is a front elevational view of a collection bag with a bactericide valve in its upright and closed orientation;

FIG. 2 is a front elevational view of the bactericide valve in a downward orientation from a collection bag;

FIG. 3 is a cross-sectional view of the bactericide valve in a closed configuration;

DESCRIPTION OF THE PREFERRED EMBODIMENTS

Figure 4:
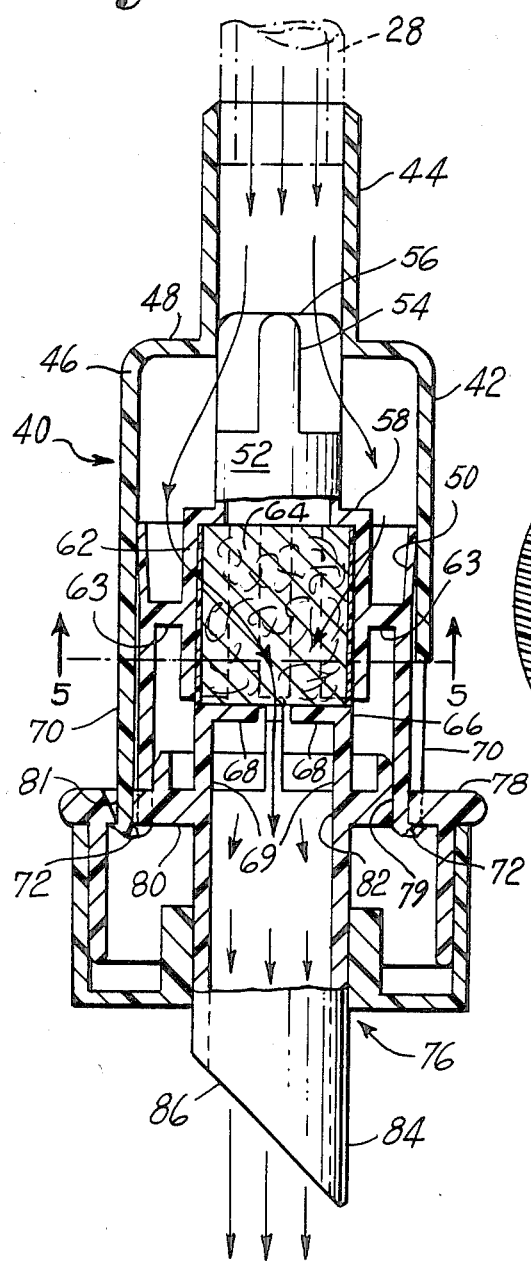
FIG. 4 is a view similar to FIG. 3, with the valve in an open configuration.
Figure 5:
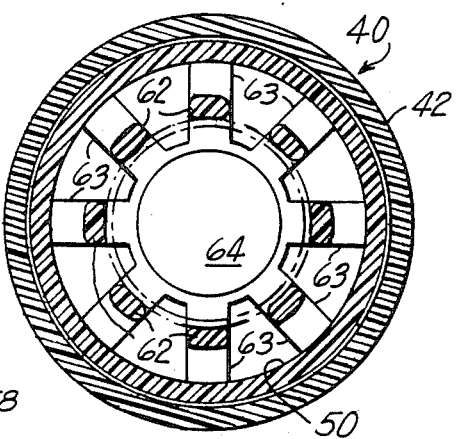
FIG. 5 is a view taken along the lines 5—5 of FIG. 3.

Referring now to the drawings in detail and particularly to FIG. 1 there is shown therein a liquid collection system 10 comprising a collection bag 12. The collection bag 12 may have a front wall 14 of flexible material and a back wall 16 of flexible material, such as a suitable plastic, with a front wall 14 and the back wall 16 being joined at their periphery in order to define a chamber 18 between the forward front wall and the back wall 16. The bag 12 may have a connector 20 secured to an upper portion of the front wall 14 such that the connector 20 communicates with the chamber 18. A downstream end 22 of a drainage tube 24 is secured to the connector 20, such that the drainage tube 24 communicates through the connector 20 with the chamber 18. The bag 12 may have a filter 26 of an air pervious, bacteria impervious material, such as known in the art, to permit passage of air from the atmosphere into the chamber while preventing the passage of bacteria from the atmosphere into the chamber 18.

During use of the bag 12, a catheter (not shown) has a distal end which is passed through the urethra of a patient until the distal end of the catheter is located in the patient's bladder and a proximal end of the catheter located outside the patient's body is connected to an upstream end of the drainage tube 24. During catheterization, urine passes from the bladder through the catheter and this drainage tube 24 into the bag chamber 18 for retention therein. As urine collects and fills the chamber 18, it is necessary to periodically empty the urine from the chamber 18.

The collection bag 12 may have a flexible or swingable tubular section 28 secured to a lower portion thereof, which tubular section 28 is in fluid communication with a lower portion of the chamber 18. A valve assembly 40 is disposed on the distal end of the tubular section 28. The valve assembly 40 is normally closed and in the storage position, tucked into a receiving pocket 30, attached to the lower portion of the front wall 14 of the bag 12 as shown in FIGS. 1 and 2.

The valve assembly 40 comprises a housing 42 having a cylindrically shaped first portion 44 connected to the downstream end of the tubular section 28. The housing 42 may be of stepped diameter as shown in FIGS. 3 and 4. A cylindrically shaped second portion 46 of the housing 42 may have a larger diameter than the first portion 44, with an annular ridge 48 connecting the two portions. A piston 50 is slidably disposed within the housing 42, having an upstream end 52 which mates with the first portion 44 thereof. The upstream end 52 of the piston 50 comprises a vane arrangement 54 disposed radially about a central core 56. The vane arrangement 54 and core 56 abut an annular flange 58 which comprises the upstream end of a cage 60. The flange 58 and upstream end 52 is arranged to sealingly mate with the annular ridge 48 and second portion 44 of the housing 42.

The cage 60 is comprised of an annular array of generally longitudinally directed ribs 62 arranged to confine a bactericide pellet 64. The ribs 62 each have a spoke 63 to connect them to the inside of the piston 50. A second cage 66 is removably disposed against the downstream end of the ribs 62 and the pellet 64. The second cage 66 has a radial array of legs 68 and a generally annular array of longitudinally directed ribs 69 attached to the upstream end of an outlet snout 76. The snout 76 has a cylindrically shaped upstream end 78. The upstream end 78 of the snout 76 comprises a disc 80 having a central opening 82 which is in fluid communication with the cage 60 and the bactericide pellet 64 disposed therein. The disc 80 also has an annular array of openings 81 therearound. The first portion 44 of housing 42 has a plurality of longitudinally directed legs 70 which slidingly mate with the annular array of openings 81 in the disc 80 on the upstream end 78 of the snout 76. The piston 50 has a plurality of fingers 72 on its downstream edge which each releasably snap into an opening 79 in the disc 80. The snout 76 has a downstream end 84 of generally cylindrical configuration, which is attached to the disc 80. The downstream end 84 of the snout 76 defines an opening 86 through which fluid may be discharged when the valve assembly 40 is in the open condition.

Axial motion of the piston 50 within the housing 42 acts to open the valve 40 to discharge urine from the chamber 18 of the collection bag 12 when the valve is in a downward orientation, as shown in FIG. 2. Urine is permitted to flow out the tubular section 28, then between adjacent vane arrangement 54 and between adjacent ribs 62 of the cage 60, "washing" over dissolving the moistened bactericide pellet 64 then between the legs 68 of the second cage 66 to be discharged out the opening 82 in the upstream end of the snout 76 and out the downstream opening 86 therein as shown by the arrows in FIG. 4.

The valve assembly 40 is closed by axially pushing the piston 50 so that its upstream end 52 including the flange 58 sealingly mates with the annular ridge 48 and inner surface of the housing 42. The bactericide pellet 64 prevents retrograde contamination of urine within the valve assembly 40 after it has been closed. This prevents contamination of the collection bag 12 and prevents subsequent contamination of a patient to whom the collection bag 12 is attached. The bactericide pellet 64 may be changed or replaced by unattaching the distal ends of the fingers 72 of the piston 50 from the openings 79 in the upstream end of the snout 76, permitting re-use of the valve 40, once the original pellet 64 has fully dissolved, deteriorated or become unusable.

Thus there has been shown a novel valve arrangement for a medical liquid collection bag, which valve arrangement helps prevent contamination of the collection bag after the valve has been closed and returned to its storage position.

I claim:

1. A liquid collection system for collecting and discharging fluids from a patient, comprising:
   a collection bag having a chamber for collection of liquid;
   a tubular section in fluid communication with a lower portion of said chamber;
   a valve assembly means having a valve seat and valve assembly on said tubular section having a means for opening and closing off any flow of liquid around a bactericide element in said valve means and said valve seat upstream of said bacteriacide element, downstream from said collection bag, said valve assembly also including a piston slidably disposed in a housing, said piston having a cage for enclosing said bactericide element in which fluid, when released from said collection bag, washes over said bactericide element when said valve means is opened, and stops the wash over of said bactericide element when said valve means is closed, whereby retrograde contamination to said system is minimized.

2. A liquid collection system as recited in claim 1, wherein a discharge means is releasably attached to the downstream end of said piston.

3. A liquid collection system as recited in claim 2, wherein said discharge means defines the downstream end of said cage.

4. A liquid collection system as recited in claim 2, wherein said piston has an annular flange and upper portion therein which is matable with an annular flange and inner wall portion of said housing, to provide means for shutting off said valve means when said annular flanges are moved towards with one another.

5. A liquid collection system as recited in claim 2, wherein said cage may be opened by removing said discharge means from the downstream end of said piston, to permit replacement of said bactericide element therein.

6. A liquid collection system as recited in claim 5, wherein said discharge means snaps into and out of the downstream end of a cylindrically shaped member of said piston.

7. A liquid collection system as recited in claim 7, wherein said cages comprise an annular array of longitudinally directed ribs, permitting fluid flow therebetween.

8. A liquid collection system as recited in claim 2, wherein liquid still in the valve means as it is being closed will be disinfected by said bactericide element.

* * * * *